United States Patent [19]

Beertsen et al.

[11] Patent Number: 5,674,725
[45] Date of Patent: Oct. 7, 1997

[54] IMPLANT MATERIALS HAVING A PHOSPHATASE AND AN ORGANOPHOSPHORUS COMPOUND FOR IN VIVO MINERALIZATION OF BONE

[75] Inventors: Wouter Beertsen, Santpoort Zuid; Theo van den Bos, Zeist, both of Netherlands

[73] Assignee: British Technology Group Limited, London, England

[21] Appl. No.: 470,952

[22] Filed: Jun. 6, 1995

Related U.S. Application Data

[63] Continuation of Ser. No. 162,049, Dec. 8, 1993.

[30] Foreign Application Priority Data

Jul. 11, 1991 [EP] European Pat. Off. .............. 91306305

[51] Int. Cl.$^6$ .......................... A61F 13/00; C12N 11/00; C12N 11/14; C12N 11/16
[52] U.S. Cl. .......................... 435/174; 424/422; 424/423; 435/176; 435/177; 435/181
[58] Field of Search .................................. 424/422, 423; 435/174, 181, 176, 177

[56] References Cited

U.S. PATENT DOCUMENTS

| | | | |
|---|---|---|---|
| 4,394,370 | 7/1983 | Jefferies | 424/15 |
| 4,409,332 | 10/1983 | Jefferies et al. | 435/188 |
| 4,698,326 | 10/1987 | Sauk et al. | 514/7 |
| 4,780,450 | 10/1988 | Sauk et al. | 514/2 |
| 4,932,973 | 6/1990 | Gendler | 623/16 |
| 4,975,526 | 12/1990 | Kuberasampath | 530/350 |
| 5,001,169 | 3/1991 | Nathan et al. | 523/113 |
| 5,011,691 | 4/1991 | Oppermann et al. | 424/423 |

FOREIGN PATENT DOCUMENTS

| | | |
|---|---|---|
| 8902155 | 3/1991 | Netherlands . |
| 0 055 848 | 3/1981 | United Kingdom . |

OTHER PUBLICATIONS

Beertsen et al, "Alkaline Phosphatase . . .", 1991, pp. 176–181.
Beertsen et al, "Calcification of Dentinal Collagen", 1989, pp. 159–171.
Beertsen et al. "Alkaline phosphatase . . . " Journal of Dental Research, vol. 70 No. 3, Mar. 1991, pp. 176–181.
Beertsen et al. "Calcification of dentinal . . . " Matrix, vol. 9 No. 2, Mar. 1989, pp. 159–171.
Chemical Abstracts #78947m, vol. 97 No. 10, 6 Sep. 1982, p. 425.

*Primary Examiner*—David M. Naff
*Assistant Examiner*—Deborah Ware
*Attorney, Agent, or Firm*—Nixon & Vanderhye

[57] ABSTRACT

The combination of a phosphatase enzyme with a biocompatible carrier material produces materials which are useful in the repair of the skeleton and the promotion of new bone growth. The combination preferably involves covalent coupling between the enzyme and the carrier. The preferred carrier materials include fibrillar collagen and may be obtained by the demineralization of calcified tissues. The materials may include phosphoproteins or dentinal phosphophoryns which may be residual or may be added during the preparation of the materials. The incorporation of other organophosphates and inorganic phosphates may improve the rate of mineralization especially in older animals.

14 Claims, 1 Drawing Sheet

IMPLANT MATERIALS HAVING A PHOSPHATASE AND AN ORGANOPHOSPHORUS COMPOUND FOR IN VIVO MINERALIZATION OF BONE

This is a Rule 60 continuation of application Ser. No. 08/162,049, filed 8 Dec. 1993.

BACKGROUND OF THE INVENTION

This invention relates to novel materials useful in the restoration and repair of the skeletal system, to processes for their production and to novel methods for the repair of the skeleton which utilise them.

There are a variety of surgical procedures used in man and animals to repair the skeleton. These include the healing of fractures by insertion of an implant to stabilise and facilitate healing of the fracture, the implantation of bone substitute materials, especially in those areas of the body which show a low intrinsic tendency to heal and the insertion of an implant which serves as a membrane to regenerate supportive tissues. The materials used as implants are ideally biocompatible and of a nature such as will promote the growth of bone.

The possible role of the enzyme alkaline phosphatase in promoting the calcification of bone has been postulated for many years. Recent studies notably an in vitro study reported by Beertsen and Van Den Bos (Matrix Vol. 9 1989 p159-171) have tended to support the proposition that alkaline phosphatase may be involved in the initiation of the calcification process apparently by virtue of its acting so as to raise the local concentration of phosphate ions.

However, the relevance of such in vitro mineralization studies to the situation in vivo has been questioned, particularly in view of the relatively high concentrations of phosphate esters used in the in vitro studies and also because the rate of hydrolysis of the phosphate esters at physiological pH levels would be expected to be too low to be relevant to the process of mineralization.

U.S. Pat. No. 4,394,370 describes a bone graft material which comprises a complex of reconstituted collagen and either demineralized bone particles or a solubilised bone morphogenetic protein fabricated as a sponge. These sponges may be complexed with bovine intestinal alkaline phosphatase. A concentration of 15 mg per gram of collagen dispersion is said to eliminate all inflammatory responses to the graft material, accelerate the formation of osteoid in the graft material and aid the slow resorption of the graft enabling it to be more completely corticalised. There is no mention of any mineralization having occurred. U.S. Pat. No. 4,409,332 describes porous membrane structures based on collageneous materials which are complexed with alkaline phosphatase in order to reduce the inflammatory reaction produced when these membranes are introduced into the body.

DESCRIPTION OF THE INVENTION

We have now discovered that novel materials useful in the repair of the skeleton may be produced by combining a biocompatible carrier material with a quantity of a phosphatase enzyme such as will promote mineralization. The level of enzyme activity is preferably at least 0.5 milliunits Apase per 1.0 μgm of hydroxyproline (where one unit is defined as 1 μmol p-nitrophenol released per minute from p-nitrophenyl phosphate at 37° C. and pH 10.5 using the technique described by Beertsen and van den Bos in Matrix, Vol. 9/1989, p161).

Biocompatible carrier materials may themselves mineralize at least to some degree if used to repair the skeleton and allowed to remain in situ for an extended period. The materials of this invention promote mineralization of the implant so that it can be readily detected within seven days and have practical utility in the repair of the skeleton.

The novel materials are stable products which when used to repair the skeleton undergo mineralization and may serve to promote the growth of new bone. Accordingly, from one aspect this invention provides a novel material useful in the repair of the skeleton which comprises a phosphatase enzyme combined with a bio-compatible carrier material and having a level of enzyme activity as will promote mineralization.

The phosphatase enzyme is preferably an alkaline phosphatase enzyme (hereinafter for convenience "APase"). APase is normally obtained by extraction from human or animal tissue. The enzyme is a cell surface glycoprotein which is capable of hydrolysing a variety of monophosphate esters. Three main forms of APase are distinguished; liver/bone/kidney; placental and intestinal and all of these forms are useful in this invention.

The carrier material may comprise any biocompatible material which is capable of combining with the enzyme. Preferably, the combination is brought about by incubating the carrier with the enzyme in the presence of a coupling agent which is capable of covalently bonding with the carrier and with the enzyme. Suitable coupling agents are those which are capable of bonding to the enzyme without significantly reducing its biological activity. A wide variety of polyfunctional compounds may be useful. The coupling agents used to form the preferred materials of this invention will be those which are capable of bonding to the carrier material. Examples of potentially useful coupling agents include biotin-avidin; glutaraldehyde and 1-ethyl-3(3-dimethyl-aminopropyl) carbodiimide HCl. The preferred coupling agents are those which do not produce an adverse reaction when introduced into the body in particular as part of a material according to this invention. The most preferred coupling agents are the carbo-diimides and in particular the compound mentioned above.

A particularly preferred coupling agent is that known as SATA-MHS, which involves the use of a combination of succinimide-S-acetylthioacetate (SATA) and maletmidohexanoyl-N-hydroxysuccinimide (MHS). Preferably the carrier is incubated with the SATA and the enzyme with the MHS. The products of these two incubation processes are combined and allowed to react to produce an implant material.

The carrier material may be of natural or synthetic origin. A wide variety of synthetic polymers are potentially useful. A particular group of synthetic materials which may be of use are those polymers which are known to be bioabsorbable. The use of synthetic materials is also advantageous insofar as they may be flexible and capable of being formed into shaped pieces designed for particular applications.

A variety of natural materials may also be used as the carrier. In particular human or animal tissues such as bones and teeth may be useful. Calcified tissues such as bones and teeth must be demineralized before they can be used as a carrier. The materials obtained by demineralization comprise a substantial proportion of fibrillar collagen. Collagen is the major fibrous protein of many animals and may be extracted from many parts of the human or animal body. Fibrillar collagen is a preferred carrier material for use in the present invention as are materials which comprise a substantial proportion of it. An example of such a material is human or animal dura mater. The carrier materials are preferably those which are sufficiently flexible to be formed into shaped pieces. Those materials which are porous or comprise meshes of fibrillar or fibrous materials are also advantageous in that they have a larger surface area to which the enzyme may be bonded. Useful carrier material may also be formed by incorporating collagen fibres into or onto a suitable supporting material always provided that the surface of the fibres remains exposed. An example of a supporting material is natural or synthetic calcium phosphates which substances may usefully form part of the materials of this invention.

The carrier material will preferably be sufficiently flexible and sufficiently strong to be useful as an implant material. The degree of flexibility or strength may vary according to the particular application for which the material is intended. The material is preferably one which is capable of being handled and manipulated prior to and during the implantation operation. The preferred implant materials comprise at least 200 units of phosphatase per cubic centimetre. The preferred carrier materials are those which are capable of combining with this amount of enzyme. Useful materials may be produced by compression of a carrier or of a material produced by combination of a carrier and a phosphatase enzyme.

The preferred carrier materials are those having a relatively smooth surface and a densely organised fibrous structure. Such materials may exhibit osteoconductive properties, i.e. they appear to guide the migration of osteoblasts and thereby to encourage the growth of new bone.

It is also preferred that the carrier has a tubular structure, i.e. one having a series of cracks or microfractures. The enzyme is bound within these tubules and mineralization may occur in them. This is advantageous insofar as the strength of the material increases as the mineralization proceeds. Mineralization may be enhanced by pre-incubating the carrier (or the combined carrier—APase material) in a solution containing physiological concentrations of calcium and an organophosphate (e.g. a 62-glycerophosphate solution) or an inorganic phosphate. The pre-incubation appears to form nucleation centres within the carrier which after implantation in the body may grow rapidly and boost the rate of mineralization.

The carrier material is preferably one which is free from any substance which might serve to inhibit its mineralization. In the case of materials of natural origin it may be necessary to extract the material thoroughly in order to reduce the level of any inhibitor to an acceptable value. Conveniently demineralization of a calcified tissue may be effected by washing the cleaned tissue and placing it in an acid solution, e.g. of acetic or hydrochloric acid for an extended period. Preferably the resulting demineralized material is further extracted with a chaotropic agent in the presence of a chelating agent.

The demineralized material may contain residual quantities of non-collagenous proteins and insoluble phosphoproteins or dentinal phosphophoryns. The presence of bound phosphoproteins or dentinal phosphophoryns has been discovered to be efficacious in promoting the demineralization. The preferred carrier materials are those which inherently comprise such phosphoproteins or phosphophoryns or those into which such phosphoproteins or phosphophoryns have been introduced and preferably covalently bound to the carrier. Preferably the materials of this invention comprise at least 0.03 micrograms of phosphate per microgram of hydroxyproline most preferably in the form of phosphoproteins or phosphophoryns.

The novel materials of this invention may be produced by incubating the carrier with the APase in the presence of the coupling agent and optionally in the presence of an organophosphorus compound.

The coupling reaction may conveniently be carried out by introducing the carrier and the APase into a solution of the coupling agent. The reaction should be carried out under conditions which do not inactivate the APase. Conveniently allowing the reactants to stand at a temperature which is not greater than ambient and is preferably less than 10° C. for periods which will in general be at least 1 hour and may conveniently be longer, say 24 hours, will be sufficient to produce a product according to the invention.

The amount of APase present in the novel materials may vary within wide limits. Preferably the materials particularly those provided that it is sufficient to promote demineralization in the intended application will exhibit a level of enzyme activity which is at least 1.0 milliunit Apase per 1.0 μgm of hydroxyproline. The optimum amount of enzyme to be incorporated will vary with the nature of the component materials, the use to which the material is to be put, the age of the person or animal into which it is to be implanted and the concentration of inorganic phosphate present in the serum of the person or animal.

Materials comprising lower amounts of enzyme may be useful in animals which are undergoing a period of relatively rapid growth. In mature animals the implants preferably contain a higher concentration of enzyme most preferably in conjunction with phosphoproteins and phosphophoryns.

Alternatively, it is possible to promote mineralization by increasing the concentration of phosphate in the locality of the implants, e.g. by transcutaneous or intravenous administration of organophosphates or inorganic phosphates. Methods of treatment of the skeleton in order to repair it which comprise the introduction of an implant material as hereinbefore described form another aspect of this invention. Methods of treatment further comprise an increase of the level of phosphates in the locality of the implant from a preferred aspect.

The amount of coupling agent employed will simply be that required to bind the desired amount of APase. In general the coupling agent will be present in the solution in a large excess over the quantity required by stoichtometry. The presence of such excess quantities of coupling agent may act so as to cross-link the surface of the carrier. Such cross-linking may be useful in improving the mechanical properties of a carrier material. It may also be useful in regulating the biodegradability of the implant. The implant should retain its mechanical integrity during the mineralization but may usefully degrade thereafter.

The materials of this invention find use in a variety of surgical procedures. The carrier material will preferably be formed into an appropriate shape prior to it being coupled to the APase.

In particular the material finds use as an internal wound dressing to stabilise and facilitate the healing of fractures or defects of the skeleton. Following implantation it mineralizes and hardens. The novel materials may also be used as a substitute for bone and used to repair fractures by fixing the material into position and allowing it to mineralize and harden in situ. The treatment of fractures in these ways provides a further aspect of this invention.

The materials also find use in treatment processes which involve what has been termed "guided tissue regeneration".

Such procedures involve the insertion of a membrane to help regenerate supportive connective tissues in areas of the body which have been damaged by disease. The membranes currently used in this application are often not biodegradable and must be removed in a second surgical operation. The materials of this invention are advantageous in this application insofar as they are biocompatible and may be allowed to remain in situ thus avoiding the need for further surgical intervention.

BRIEF DESCRIPTION OF THE DRAWING

The present invention will not be described in more detail with reference to the following examples and with reference to FIG. 1 which shows the results of experiments described in Example 3.

EXAMPLES

Figure 1:
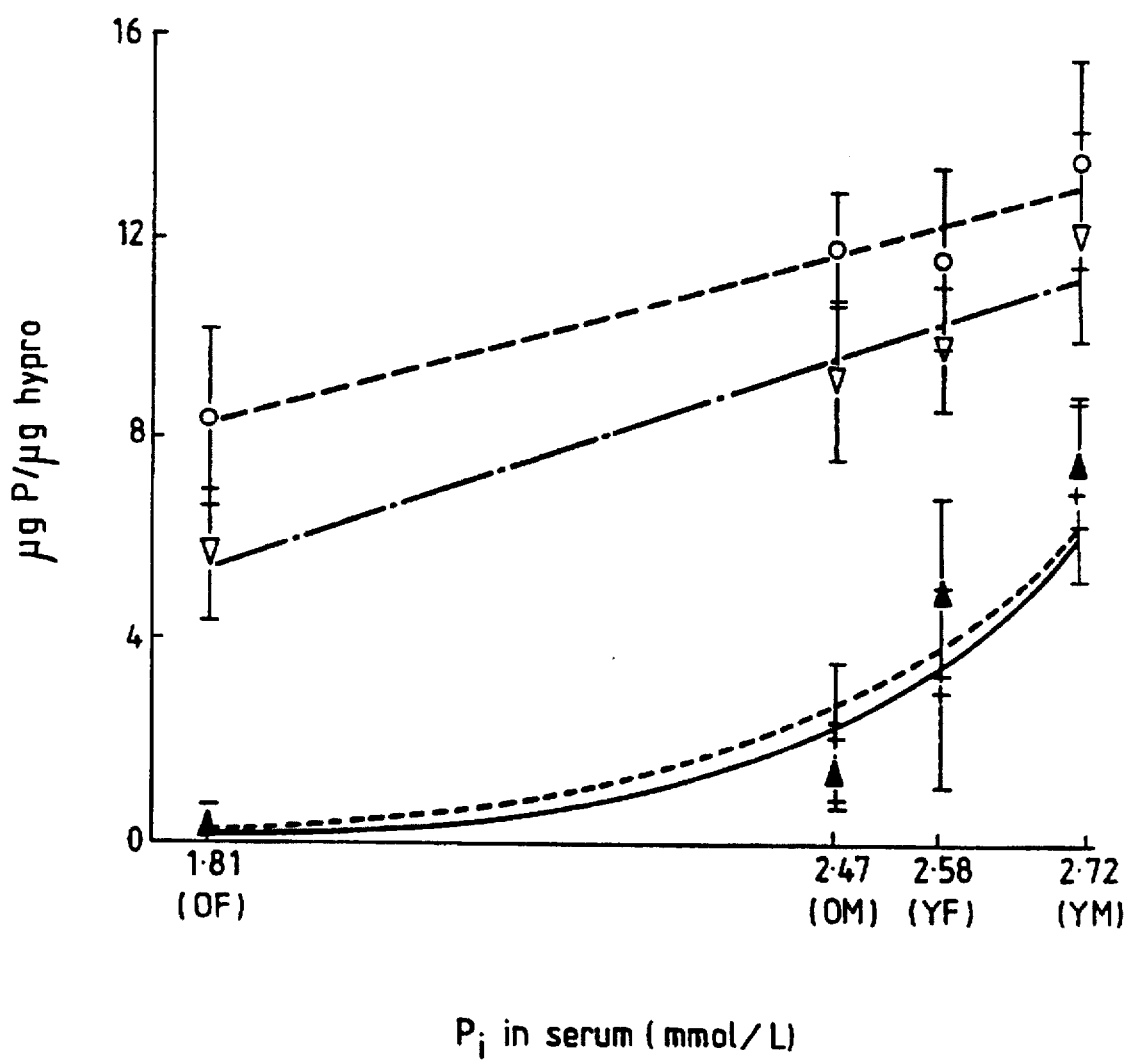

The invention is illustrated by the following examples.

Example 1

Preparation of dentinal collagen sheets.

Bovine permanent incisors were collected at the local slaughterhouse immediately after killing (age 1–3 yr) and frozen at −80° C. until use. After defrosting, the gingiva and periodontal ligament were removed and the roots cut with a diamond disk parallel to their longitudinal axis from the apex to the cervical area under constant irrigation with tap water and split with a chisel. The roots were then cleaned and freed from pulp and cementum. They were washed with ice-cold PBS in the presence of proteinase inhibitors and the outer dentin (containing the mantle dentin layer) was removed with a diamond disk under cooling with tap water.

Demineralized dentin slices (DDS) were prepared by soaking in 0.5M acetic acid or 0.6M hydrochloric acid for four weeks. Sections were cut by means of a cryotome set at 30 μm. They were then further extracted with 4M guanidine.HCl and 0.4M EDTA (pH 7.5) for three days at 4° C. Before use the DDS were washed in double-distilled water for one hour and placed in double-distilled water supplemented with antibiotics at 4° C. overnight. DDS contained 0.04 μg $PO_4$ per μg hydroxyproline.

Binding of Apase.

Bovine intestinal Apase was covalently bound to the dentinal collagen sheets by using the coupling agents glutaraldehyde or carbodiimide.

Glutaraldehyde coupling.

The DDS were incubated in PBS containing 0.1% glutaraldehyde for 2 h at 25° C. in the presence of APase (700 U per ml). The material was then extensively washed with PBS and stored at 4° C. in 0.1M glycine buffer pH 10.5 containing 1 mM $Mg^{2+}$ and 0.1 mM $Zn^{2+}$.

Carbodiimide coupling.

The DDS were incubated for 2 days at 4° C. in 0.13M 1-ethyl-3(3-dimethylaminopropyl)carbodiimide.HCl pH 4.5 in the presence of APase (700 U per ml). They were then exhaustively washed with distilled water, with 1M NaCl in 0.1M Na-acetate pH 4.0, with distilled water, with 0.1M $NaHCO_3$ pH 8.3 and finally with distilled water. The material was stored in glycine buffer at 4° C. (see preceding paragraph). The enzyme retained its activity under these storage conditions for at least 10 months.

In vitro experiments.

In order to study the deposition of mineral in the collagen sheets as a function of time in vitro, APase-treated DDS (30 μm thickness) and their controls (treated with crosslinking agents only or heat inactivated enzyme) were incubated in Iscove Modified Dulbecco's Medium (IMDM) supplemented with 10% heat-inactivated Normal Rabbit Serum (NRS) and antibiotics for varying time periods at 37° C. Radiolabelled calcium (1 μCi [$^{45}Ca$]$Cl_2$ per well) was added and the collagen sheets monitored for uptake of the label. As phosphate source β-glycerophosphate (β-GP) was added in a concentration of 10 mM. At the end of the experiment the specimens were decalcified in 0.5 ml 1M HCl for 1 h at 37° C. Samples of 300 μl were added to Optifluor scintillation cocktail (Packard Instruments Inc.) and counted in a Packard Tricarb 4530 scintillation counter.

In vivo experiments.

APase-treated DDS was tested for its ability to calcify under in vivo conditions as follows. Female Wistar rats (about 200 g each) were anaesthetized with Hypnorm and an incision was made through the skin covering the skull following the sagittal suture. The skin was retracted so as to expose the right and left temporal muscles. A pouch was then created on either side by cutting through the insertion of the exposed muscle. DDS slices of 30 μm thickness and 1 cm in width, 2 cm in length were inserted into the pouches: APase-treated ones on the right side and controls on the left side. Care was taken that only a narrow rim of the implant was in contact with the muscle; its greater part (90%) was in direct contact with the dermis. The skin wound was closed with nylon sutures and allowed to heal for time periods varying from one to four weeks. The animals were then anaesthetized again, the wounded region re-opened and the implants excised. A small portion of each implant was removed together with the surrounding connective tissue and prepared for histological examination. The remaining portion was freed from surrounding tissues and used for chemical analyses.

Results

In vitro experiments.

DDS treated with APase accumulated radiolabelled calcium when incubated in the presence of β-GP. In the absence of the monophosphate ester very little [$^{45}Ca$] was found in the dentin. When incorporation of the label in carbodiimide-treated specimens was followed as a function of time, a rapid influx of [$^{45}Ca$] was observed during the first day. Thereafter, a more gradual increase was noted. Control sheets, treated with carbodiimide without enzyme, remained almost free of radioactivity. APase-containing slices hardened rapidly and stained positively with the Von Kossa method. The mineral was laid down in the form of needle-like crystallites in close association with the collagen fibrils of the carrier and (according to X-ray diffraction) exhibited hydroxyapatite-like characteristics.

In vivo experiments.

Healing of the skin wounds was uneventful. Inspection of the sites of implantation during the re-entry procedure revealed that, particularly with the carbodiimide-treated implants, the surrounding tissues were rich in collagen and not inflamed. The glutaraldehyde-treated implants, however, were often surrounded by a richly vascularized, somewhat oedamatous connective tissue. In both implant types the (APase-coupled) DDS had become hard within one week and acquired an opaque appearance. Control specimens were soft and translucent upon macroscopic inspection.

Chemical analysis demonstrated that mineral uptake by APase-treated DDS was very rapid at the early stages after installment. As time progressed a further increase occurred with respect to the carbodiimide-treated specimens. According to linear regression analysis, this increase was statistically significant for phosphate ($p<0.05$). After 4 wk, in carbodiimide-coupled specimens the calcium content per µg hydroxyproline was about 80% of that found in normal bovine dentin, while the phosphate content was about 60%.

When expressed in terms of molar concentrations, it appeared that the Ca/P ratio in the remineralized dentin was about 2.00 for the carbodiimide-treated specimens and 1.80 for the glutaraldehyde-treated ones. In normal bovine dentin this ratio was 1.7

Example 2

A series of implant materials were prepared using the materials and techniques described in Example 1. The coupling agent was 1-ethyl-3(3-dimethylaminopropyl)carbodiimide.

Forty female Wistar rats (body weight, ca. 200 g) were anesthetized with Hypnorm. An incision was made through the skin parallel to the sagittal suture. The skin covering the right and left parietal bones was reflected so as to expose the cranial vault from the frontal to the occipital region. A periosteal flap was raised on either side following incisions along the sagittal, frontal and occipital sutures. By use of a slowly rotating trephine bur (Ø 1.8 mm) mounted in a dental handpiece, two through and through defects were made in each of the parietal bones leaving a distance of about 1.0 to 1.5 mm in between. To prevent overheating during surgery, the tissues were kept moistened with physiological saline. Special care was taken not to injure physically the underlying dura mater.

The wounds were covered with a graft, one on either side of the skull, each measuring 0.5 cm in width and 0.8 cm in length. On the right side an APase-containing one was implanted, on the left side a control one (no enzyme). The periosteum and skin were closed. The animals were killed by decapitation at the following time intervals post surgery: 3 weeks, 6 weeks, 9 weeks and 12 weeks. The calvariae were dissected out and immersed in a solution of 4% paraformaldehyde and 1% glutaraldehyde in 0.1 mol/L Na-cacodylate buffer (pH 7.4) for 24 h. The specimens were postfixed in 1% $OsO_4$ and embedded in epoxy resin.

Each skull half was oriented on the microtome so as to section the two wounds in the same plane, perpendicular to the cranial vault. Sections were stained with methylene blue or according to the Von Kossa method. From each specimen one methylene blue stained section was taken from the central area of the two defects and used for histomorphometric analysis.

Ultrathin sections were cut with a diamond knife, stained with uranyl acetate and lead citrate and examined in a Zeiss EM 10C electron microscope.

Histomorphometric analysis.

Of each selected section a tracing was made by using a sign prism at a magnification of ×173. The mineralised area of each graft was measured by using an X-Y device and expressed as percentage of the total area occupied in the plane of sectioning. Also the thickness of the grafts was assessed and the length of direct contact with newly formed bone was measured, both along the inner (directed towards the skull) and outer (directed towards the skin) aspects of the grafts.

Results

As shown histochemically, APase-activity in the enzyme-treated implants was bound to the wall of the dentinal tubules and the outer aspects of the sheets. The distribution of the activity was uniform, in that along the entire length of the sheets the same staining pattern was seen. Sections of control sheets that were incubated with the crosslinking agent in the absence of APase did not show any histochemical staining. Based on the conversion rate of p-nitrophenylphosphate, the enzyme-treated collagen sheets contained 0.95±0.24 mU of enzyme per µg hydroxyproline.

Healing of the surgical sites was uneventful in that the inflammatory response of the tissues surrounding the grafts, as assessed macroscopically, was negligible. More specifically, there were no signs of edema, redness and swelling. Macroscopic inspection and careful palpation with tweezers of the implants after fixation revealed that the APase-containing grafts had hardened, whereas the controls had remained soft.

Light and electron microscopic examination demonstrated that the experimental grafts had accumulated mineral during the course of the experiment. Within the first three weeks following implantation about 55% of their sectioned area was occupied by mineral. Thereafter, the amount of mineral showed a slight further increase to about 70–80%. Areas that had remained free of mineral were often near the edges where the grafts were in contact with the connective tissues of the overlying periosteum. No conspicious differences in mineral density were observed between parts of the graft overlying the osseous defects and those overlying intact bone.

In the control grafts no substantial mineralization could be detected up to and including the nine week time interval. Twelve weeks after surgery, however, some of the control specimens contained mineralized areas, more or less randomly distributed along the grafts. On the average these areas occupied about 20% of the grafted material.

In all cases the mineral was deposited as small crystals in close association with the collagenous fibrils constituting the grafts. The dentinal tubules had remained open and along the edges of the grafts no layers of mineralized material had been deposited in the adjacent periosteum. Also no signs of cartilage formation were found.

As the grafts mineralized osteoblasts appeared which contained an extensive Golgi apparatus and rough endoplasmic reticulum. In between the osteoblast layer and the mineralized part of the graft osteoid and bone was deposited. Although no measurements were carried out on the strength of attachment between implant and bone, the orientation of cracks due to sectioning artifacts in the mineralized matrices gave some indication. They were seldom found along the borderline between the two. Usually they passed the bone-implant boundary.

All these phenomena were particularly apparent along the inner aspect of the enzyme-treated collagen sheets, facing the calvarial bone. Along the outer aspect directed towards the ectoctranial periosteal layer very little, if any, bone was formed. Correlation analysis showed that, as mineralization of the grafts increased, also the length of direct bone contact along its inner aspect tended to increase (correlation coefficient r=0.53, n=37; p<0.005).

Also in the control implants a positive correlation was found between their degree of mineralization and the length of direct contact with newly formed bone (r=0.45, n=37; p<0.01). However, the extent to which the grafts were associated with bone was far less than on the experimental side of the skull. The difference among the two sides proved to be statistically significant (p<0.01).

Little inflammatory reactions were seen in the tissues surrounding the grafted material. More specifically, plasma cells were virtually absent and polymorphonuclear leukocytes and lymphocytes were very sparse. However, all implants showed evidence of a mild foreign body reaction, in that macrophages and multinucleated giant cells were present along the implant surfaces, except where the implants were in direct contact with newly formed bone. This was the case on the control as well as the experimental sides. The number of giant cells along the grafts was approximately the same for the experimentals and controls (Wilcoxon-signed-ranks test, $p>0.05$) and they were not specifically associated with either mineralized or non-mineralized parts of the grafts.

Despite the presence of multinucleated giant cells in relation to the grafts, no major resorption of the implants had occurred, neither in the non-mineralized nor in the mineralized areas. Evidence for this was provided by the observation that the grafts kept their overall width during the course of the experiment (32 μm) and were not invaded to a great extent by resorbing cells. Yet, at various sites cells were seen with cytoplasmic processes penetrating deeply into the dentinal tubules. In none of the mineralized grafts osteoclasts, exhibiting ruffled borders were observed and no Howship's lacunae were seen.

Example 3

Mineralization of an implant material was studied as a function of age, sex, site of implantation and phosphoprotein content.

Male and female Wistar rats, 5 or 20 weeks old, were anesthetised and their weight determined. Sheets of material were then implanted subcutaneously in the following sites: over the skull (parietal and frontal bones), the lower back region, the wall of the abdomen. Control slices were without APase or with heat-inactivated APase. After two weeks the animals were weighed again, killed (under general anesthesia) by decapitation and the sheets taken out and analysed for phosphate content. Samples of serum were assayed for inorganic phosphate.

Preparation of material.

Two types of material were tested: one made from demineralized and guanidine-extracted bovine dentin (which still contained some covalently bound dentinal phosphophoryns: $0.035\pm0.019$ μg phosphate/μg hypro) and the other made from demineralized and guanidine-extracted bovine cortical bone ($0.005\pm0.0025$ μg phosphate/μg hypro). Slices were made as described in Example 1.

APase was bound to the collagenous carrier (mainly type I collagen) according to the SATA-MHS coupling method.

A: SATA (succinimidyl-S-acetylthioacetate, Pierce) was linked to the carrier: 175 mg of collagen was incubated in 5 ml 0.05M phosphate pH 7.5, 1 mM EDTA and 500 μl SATA (15 mg/ml dimethylsulfoxide) for 30 min at room temperature. The collagen sheets were then washed four times with phosphate buffer. Just before coupling collagen-SATA slices to APase-MHS (see below), the slices were deacetylated by incubation in a solution of 5 ml 0.05M phosphate pH 7.5, 1 mM EDTA and 500 μl deacetylation solution (1.75 g Hydroxylamine HCl and 0.475 g EDTA in 50 ml 0.05M phosphate pH 7.5) at room temperature. After 2 h incubation the solution was decanted.

B: MHS (maletmidiohexanoly-N-hydroxysuccinimide or N-succinimidyl-6-maleidocaproate, Fluka) was coupled to APase as described by Peeters et al., (Immunol. Methods 120, 133–143, 1989):

To 10 mg APase/ml 0.05M phosphate pH 8.0 was added 1.54 mg MHS/40 μl dimethyl-formamide. After 5 min incubation at room temperature 1 ml 0.05M phosphate pH 6.0 was added and the maleimidated APase separated from the smaller, organic molecules by means of a Sephadex G-25 column (10×1 cm). The column was eluted with 0.05M phosphate pH 6.0 and fractions of 1.5 ml were collected. The APase activity containing fractions in the void volume were pooled (ca 4 ml).

C: Reaction between collagen-SATA slices and APase-MHS:

To the deacetylated collagen-SATA slices 4 ml of APase-MHS in 0.05 M phosphate pH 6.0 were added and the slices incubated for 4 h at room temperature. Afterwards the solution was decanted and the slices washed as described in Example 1. The slices were stored in glycine buffer at 4° C. The dentinal collagen slices contained $1.36\pm0.28$ mU APase/μg hypro, the bone collagen slices $2.39\pm0.41$ mU APase/μg hypro.

Results

The results of this experiment are summarised in FIG. 1. The symbols used are:

| | | | |
|---|---|---|---|
| -0- | dentin/skull | OF | older females |
| -V- | dentin/abdomen | OM | older males |
| -Δ- | bone/abdomen | YF | younger females |
| -+- | bone/skull | YM | younger males |

The results show that mineralization of the collagen slices (Y axis) was greatly influenced by sex, age and phosphoprotein (PP) content. Especially the bone-derived slices (low in PP content) proved to be quite low in their degree of mineralization when compared with the dentin-derived slices (relatively high in PP content). Male rats showed more influx of mineral (as measured by phosphate content) than females. The younger animals showed more mineral uptake than the older ones. A high correlation was found between mineralization of the implant and the concentration of inorganic phosphate in the serum (X axis).

Only minor differences were seen between the various implantation sites, the dentin-derived slices in the skull showing a slightly higher degree of mineralization than those in the back and the abdomen. No differences were seen between the lower back region and the abdominal wall.

All control slices had remained free of mineral within the 2 week experimental period.

We claim:

1. A material which comprises a biocompatible carrier having a densely organized fibrous structure, said carrier comprising fibrillar collagen, in combination with a phosphatase (Apase) in an effective amount having an enzyme activity of at least 1.0 milliunit Apase per 1.0 microgram (ugm) of hydroxyproline for promoting in vivo mineralization of the material, said material further comprising an organophosphorus compound.

2. The material according to claim 1, wherein the phosphatase is an alkaline phosphatase.

3. The material according to claim 1 wherein said organophosphorus compound is a dentinal phosphophoryn.

4. The material according to claim 1 wherein said organophosphorus compound is a phosphoprotein.

5. The material according to claim 4 wherein the biocompatible carrier contains at least 0.03 micrograms of phosphate per microgram of hydroxyproline.

6. The material according to claim 1 wherein the biocompatible carrier is produced by the demineralization of calcified human or animal tissue.

7. The material according to claim 1 wherein the biocompatible carrier comprises demineralized dentin or demineralized bone.

8. The material according to claim 1 which comprises at least 200 units of the phosphatase per cubic centimetre.

9. The material according to claim 1 wherein the phosphatase is covalently bonded to the carrier.

10. A process for the production of a material according to claim 9, which comprises incubating the biocompatible carrier and the phosphatase in a solution of a polyfunctional coupling agent.

11. The process according to claim 10, wherein the incubation is carried out in the presence of an organophosphorus compound additional to any organophosphorus compound present in the carrier.

12. The process according to claim 10, wherein the incubation is carried out in the presence of calcium and inorganic phosphate ions additional to any calcium or inorganic phosphate ions present in the carrier.

13. An implantable composition suitable for use in the repair of a skeleton, which comprises a biocompatible carrier having a densely organized fibrous structure, said carrier comprising fibrillar collagen, in combination with a phosphatase (Apase) in an effective amount having an enzyme activity of at least 1.0 milliunit Apase per 1.0 microgram (μgm) of hydroxyproline for promoting in vivo mineralization of the composition, said composition further comprising an organophosphorus compound.

14. The composition according to claim 13, wherein said phosphatase is an alkaline phosphatase.

\* \* \* \* \*

UNITED STATES PATENT AND TRADEMARK OFFICE

CERTIFICATE OF CORRECTION

PATENT NO.    : 5,674,725
DATED         : October 7, 1997
INVENTOR(S)   : BEERTSEN It is certified that error appears in the above-identified patent and that said letters patent is hereby corrected as shown below:

On the title page, Item [30], insert

--Jul. 9, 1992    [PCT]    PCT/GB92/01247-- below "Jul. 11, 1991  [EP]  European Pat. Off.....91306305"

Column 10, line 46, delete "(Apase)".

Column 12, line 5, delete "(Apase)".

Signed and Sealed this

Twenty-ninth Day of June, 1999

*Attest:*

Q. TODD DICKINSON

*Attesting Officer*     Acting Commissioner of Patents and Trademarks